US010223497B2

(12) United States Patent
Pradeep et al.

(10) Patent No.: US 10,223,497 B2
(45) Date of Patent: Mar. 5, 2019

(54) INFANT LEARNING RECEPTIVITY DETECTION SYSTEM

(71) Applicant: Smilables Inc., Berkeley, CA (US)

(72) Inventors: Anantha Pradeep, Berkeley, CA (US); Ratnakar Dev, Berkeley, CA (US); Thomas Robbins, Berkeley, CA (US)

(73) Assignee: SMILABLES INC., Berkeley, CA (US)

( * ) Notice: Subject to any disclaimer, the term of this patent is extended or adjusted under 35 U.S.C. 154(b) by 768 days.

(21) Appl. No.: 14/681,906

(22) Filed: Apr. 8, 2015

(65) Prior Publication Data

US 2016/0292576 A1  Oct. 6, 2016

Related U.S. Application Data

(63) Continuation of application No. 14/679,010, filed on Apr. 5, 2015, now abandoned.

(51) Int. Cl.
| | |
|---|---|
| G06N 99/00 | (2010.01) |
| G06F 19/00 | (2018.01) |
| A61B 5/053 | (2006.01) |
| A61B 5/01 | (2006.01) |
| A61B 5/11 | (2006.01) |
| A61B 5/16 | (2006.01) |
| A61B 5/00 | (2006.01) |
| G16H 50/20 | (2018.01) |
| A61B 3/00 | (2006.01) |
| A61B 3/113 | (2006.01) |

(52) U.S. Cl.
CPC ............... *G06F 19/00* (2013.01); *A61B 5/01* (2013.01); *A61B 5/0533* (2013.01); *A61B 5/11* (2013.01); *A61B 5/165* (2013.01); *A61B 5/4809* (2013.01); *A61B 5/681* (2013.01); *A61B 5/7275* (2013.01); *G06F 19/3418* (2013.01); *G06N 99/00* (2013.01); *A61B 3/0033* (2013.01); *A61B 3/113* (2013.01); *A61B 5/1113* (2013.01); *A61B 5/1118* (2013.01); *A61B 2503/04* (2013.01); *A61B 2560/0242* (2013.01); *A61B 2562/0219* (2013.01); *G16H 50/20* (2018.01)

(58) Field of Classification Search
CPC .................................. G06N 99/00; A61B 5/01
See application file for complete search history.

(56) References Cited

U.S. PATENT DOCUMENTS

| | | | |
|---|---|---|---|
| 7,261,690 B2 * | 8/2007 | Teller | A61B 5/02055 128/905 |
| 2008/0187893 A1 * | 8/2008 | Blaustein | G09B 7/02 434/236 |
| 2015/0094544 A1 * | 4/2015 | Spolin | A61B 5/7275 600/301 |

OTHER PUBLICATIONS

DS Messinger et al., "Early interactive emotional development", InDevelopment and Learning, 7th IEEE Int'l Conf. on, Aug. 9, 2008, pp. 232-237).*

* cited by examiner

*Primary Examiner* — Vincent Gonzales
(74) *Attorney, Agent, or Firm* — Kwan & Olynick LLP

(57) ABSTRACT

Provided are mechanisms and processes for more effectively monitoring infants to enhance caregiving and infant development. A system may include an infant monitoring device and a monitoring hub. The infant monitoring device includes sensors that gather measurement data. The monitoring hub receives the measurement data and analyzes the measurement data in relation to a learning receptivity model obtained from a remote platform. The measurement data is analyzed to predict a time and duration when an infant associated with the infant monitoring device will be receptive to learning.

20 Claims, 10 Drawing Sheets

INFANT LEARNING RECEPTIVITY DETECTION SYSTEM

CROSS-REFERENCE TO RELATED APPLICATIONS

The present invention claims priority of pending U.S. patent application Ser. No. 14/679,010 filed Apr. 5, 2015 which is incorporated herein by reference in its entirety.

TECHNICAL FIELD

The present disclosure relates to infant monitoring devices. In one example, the present invention relates to mechanisms for providing a wearable infant monitoring device.

BACKGROUND

Conventional infant monitoring systems include audio or visual monitors that remotely collect aural or visual information and transmit this information to another device that allows a caregiver, such as a parent, to view or hear the information. For instance, a microphone may be placed in proximity to the infant, such as on a night stand or table, and a remote speaker may be placed in proximity to a caregiver in another location such as another room. This allows the caregiver to hear the infant's cries, etc. Some monitoring systems include a video camera that is positioned to record movement and position of an infant. A caregiver can view the video of the infant from a remote device, such as a dedicated monitoring device or a smart phone.

Although conventional systems allow caregivers to monitor sounds and video of a baby from a remote device, these monitoring systems are limited to providing only rudimentary monitoring of an infant. Essentially, the monitoring systems allow a caregiver to hear and see the infant from a different location, such as from another room within a home. A caregiver must guess from the sounds and sights transmitted through the monitoring system about the infant's needs, mood, health, and well-being. Some wearable devices provide rudimentary heartrate and temperature information about an infant to a caregiver. However, current monitoring systems are extremely limited in nature. Caregivers can greatly benefit from a more robust monitoring system to improve the care and development of their infants.

OVERVIEW

Provided are mechanisms and processes for more effectively monitoring infants to enhance caregiving and infant development. A system may include an infant monitoring device and a monitoring hub. The infant monitoring device includes sensors that gather measurement data. The monitoring hub receives the measurement data and analyzes the measurement data in relation to a learning receptivity model obtained from a remote platform. The measurement data is analyzed to predict a time and duration when an infant associated with the infant monitoring device will be receptive to learning.

These and other embodiments are described further below with reference to the figures.

DESCRIPTION OF EXAMPLE EMBODIMENTS

Figure 1:
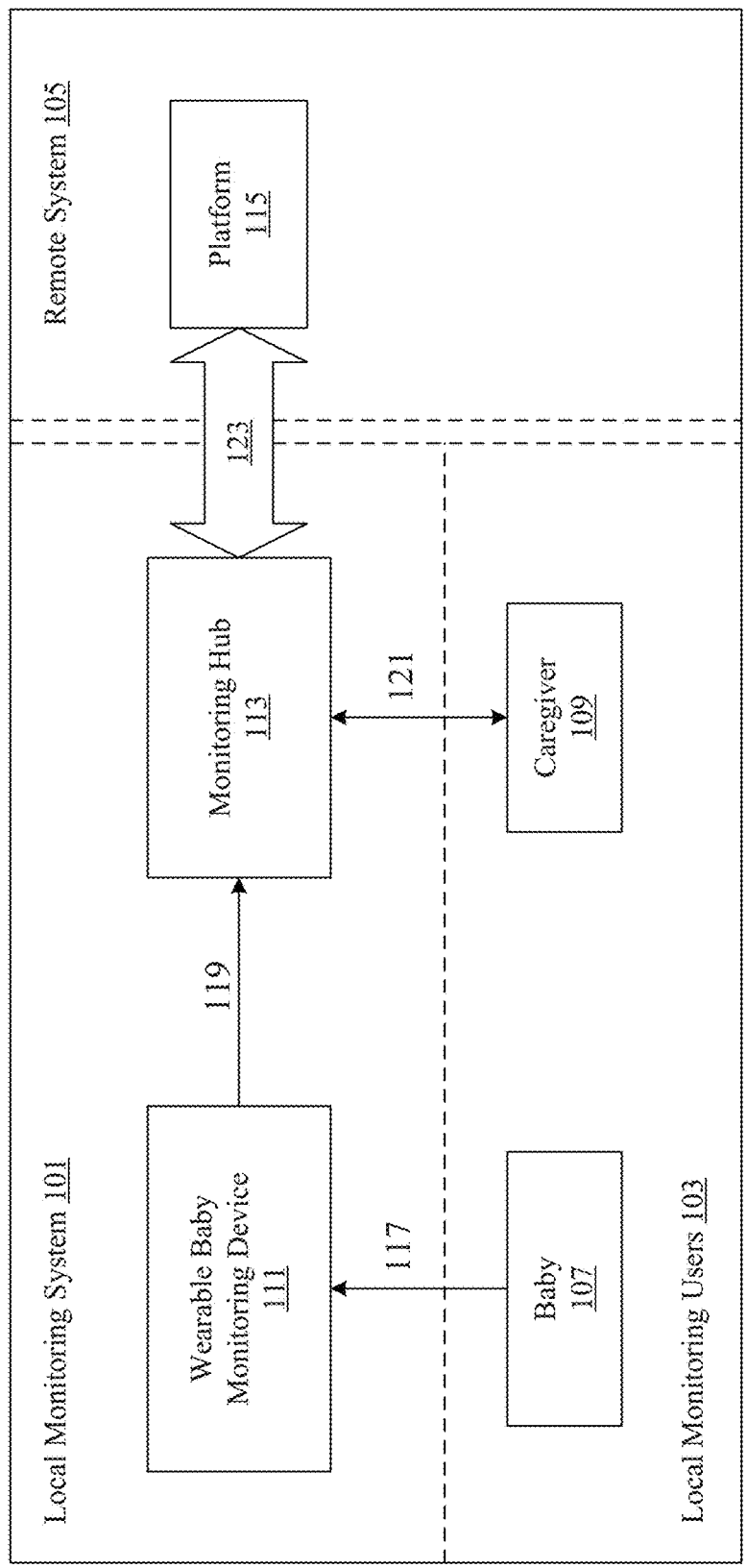
FIG. 1 is a diagrammatic representation of one example of an infant monitoring system.

Reference will now be made in detail to some specific examples of the invention in order to provide a thorough understanding of the presented concepts. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

Various techniques and mechanisms of the present invention will sometimes be described in singular form for clarity. However, it should be noted that some embodiments include multiple iterations of a technique or multiple instantiations of a mechanism unless noted otherwise. Furthermore, the techniques and mechanisms of the present invention will sometimes describe two entities as being connected. It should be noted that a connection between two entities does not necessarily mean a direct, unimpeded connection, as a variety of other entities may reside between the two entities. Consequently, a connection does not necessarily mean a direct, unimpeded connection unless otherwise noted.

Conventional systems for baby monitoring typically allow caregivers to monitor audio and/or video of an infant from a remote device such as a speaker or portable device. However, these monitoring systems are limited to providing only rudimentary monitoring of an infant. Essentially, the monitoring systems allow a caregiver to hear and see the infant from a different location, such as from another room within a home. A caregiver must guess from the sounds and sights transmitted through the monitoring system about the infant's needs, mood, health, and well-being. Once the caregiver goes to the infant, the monitoring system is no longer useful.

Some wearable devices provide rudimentary heartrate or temperature information about an infant to a caregiver. However, all of these current monitoring systems are extremely limited in nature. Caregivers can greatly benefit from a more robust monitoring system to improve the care and development of their infants.

Various embodiments of the present disclosure relate to providing an infant monitoring device that is wearable by an infant. For instance, a wearable baby monitoring device can gather various measurements associated with the baby, such as motion, temperature, position, arousal, etc. These measurements can be transmitted to a monitoring hub that can process the data into useful information that can be provided to one or more caregivers. In some examples, environmental sensors can collect additional measurement data, such as audio levels and video data, which can also be transmitted to the monitoring hub. In some embodiments, the monitoring hub may include interaction with remote servers configured to aggregate information from multiple wearable baby monitoring devices in disparate locations.

According to various examples, the monitoring hub can process the measurement data to provide information about an infant such as sleep, mobility, stress, position, comfort, health, vigilance, articulation, receptivity to learning, baby well-being, presence of caregiver, environmental conditions, safety of the baby, emotional state of the baby, emotional receptivity, receptivity to learning, etc. In some examples, this information can be provided to a caregiver, such as through the hub directly or through a client device, such as a mobile device. Additional recommendations about care for the infant can also be provided to the caregiver by the monitoring hub, according to various examples.

In particular embodiments, the measurement data and/or processed measurement data can be transmitted to a remote platform, in various examples. This remote platform can collect measurement data and/or processed measurement data from numerous baby monitoring devices in a community. According to various embodiments, the remote platform is a remote infant developmental analysis platform. The remote infant developmental analysis platform may use this aggregated data to determine various patterns and phenomena and use this data to form additional suggestions for caregiving, teaching, etc. For instance, charts on infant growth and development can be formed with the aggregated data. These charts can then be transmitted to individual monitoring hubs and caregivers can see how their respective infants compare to the charts, etc. In other examples, measurement data can be used to develop models for when an infant is receptive to learning, etc. Information from these models can be provided to the individual monitoring hubs and can be provided to caregivers at appropriate times. In yet other examples, behavior models, etc. can be used to provide feedback to caregivers about how to make their infants more comfortable, etc.

With reference to FIG. 1, shown is a diagrammatic representation of one example of an infant monitoring system. According to various embodiments, the infant monitoring system is designed to be safe, secure, and easy to use. As shown, the system includes a local monitoring system 101 and a remote system 105. The local monitoring system includes a wearable baby monitoring device 111 and a monitoring hub 113. The remote system 105 includes a platform 115, which is designed to collect data from a community of users. In various examples, information about an infant 107 is collected at the wearable baby monitoring device 111, this information is processed at the monitoring hub 113, and models can be developed at the platform 115.

According to various embodiments, the wearable baby monitoring device 111 collects data and provides notifications. The wearable baby monitoring device 111 is an infant-friendly wearable device, which monitors baby activity and other baby related biometric measures. In one embodiment, the wearable baby monitoring device 111 is worn on the ankle of an infant and collects activity and emotional state data and receptivity to learning data. For instance, the wearable baby monitoring device 111 can collect data regarding an infant's motions, orientation, and physiology. In some examples, the target demographic for the baby is between about 0-24 months of age. Notifications can be provided at the wearable baby monitoring device 111 in some instances. For instance, an LED on the wearable baby monitoring device 111 can indicate to a caregiver 109 that the battery charge is low or that the device is currently charging, etc.

In the present example, measurement data associated with the baby is gathered by or otherwise input 117 into the wearable baby monitoring device 111. This measurement data is then transmitted 119 to a monitoring hub 113. This monitoring hub 113 can perform various functions, depending on the desired application, such as data pre-processing, ambient sensing, content cache, and baby status assessment. In some examples, the monitoring hub includes learning content and a schedule. For instance, the learning content includes information for caregivers about what to teach to an infant and the schedule can indicate when this content should be appropriately presented, such as based on age or developmental level. This learning content can be obtained from the platform 115 in some embodiments. More specifically, the platform 115 may store various libraries of data, models, schedules, etc. that can be accessed by the monitoring hub 113. For instance, the platform may store models such as an environmental suitability model (predicting a range of environmental conditions and expected infant characteristics corresponding to these environmental conditions), baby orientation model (predicting a position of a baby based on data such as motion and geoposition), learning receptivity model (predicting a time and duration when an infant will be receptive to learning), and health model (predicting a health concern such as an epileptic seizure, lying in a prone position associated with increased risk of SIDS, etc.). These models may include thresholds for making various determinations, which can trigger notifications to a caregiver. For example, an environmental suitability model can include thresholds for sound pollution, visual clutter, and/or light over-intensity, and exceeding any of these thresholds may trigger a determination that the environmental conditions are not suitable for an infant. The monitoring hub 113 can select and customize content from the library to correspond to the needs and development of a particular baby 107 being monitored. According to various embodiments, the monitoring hub 113 can also provide digital signal processing, a human interface, and data security. In some examples, development models can be evaluated at the monitoring hub 113. Additionally, model-based content adaptation can be provided at the monitoring hub 113 in some applications. Furthermore, the monitoring hub 113 may provide notifications or suggestions to a caregiver based on a determination made at the monitoring hub 113 or platform 115. For instance, if a determination is made that environmental conditions are not suitable for an infant, the monitoring hub can make suggestions including ways to reduce noise, light intensity, visual clutter, etc. In particular, suggestions may include closing windows, turning off lights, reducing the amount of toys or items in the room, etc.

Although not explicitly shown in FIG. 1, a mobile device can also be included in the local monitoring system 101. In some embodiments, the mobile device can communicate with the monitoring hub 113 and/or the wearable baby monitoring device 111. In addition, the mobile device can provide an interface to the local monitoring system 101 for the caregiver 109. For instance, the caregiver 109 may be able to view data about the baby via the mobile device, including information such as biometric data, video, audio, etc. In some examples, the mobile device can act as the monitoring hub 113 itself. According to various embodiments, the mobile device can provide data pre-processing, early warning, and remote observation. The mobile device can also include social and environmental content. In some instances, a caregiver 109 can input information about social and environmental conditions and/or the mobile device can detect various conditions using inputs such as a microphone, camera, etc. In some examples, the mobile device includes content for the caregiver about suggested social interactions or environmental augmentation or adjustments such as music, lights, etc.

According to various embodiments, a caregiver 109, such as a mother, father, nanny, babysitter, or other primary caregiver, is the primary user of the data from the wearable baby monitoring device 111. The caregiver 109 can also provide information to the system such as developmental assessments, nominal baby habits, etc., such a through a mobile device and/or the monitoring hub 113. Information can be provided to the caregiver 109 via monitoring hub 113 and/or a mobile device associated with the local monitoring system 101. For instance, adapted content, baby monitoring, and social engagement is provided through the monitoring hub 113 and/or the mobile device.

In the present example, data from the monitoring hub 113 is transmitted 123 to the platform 115. For instance, raw data, including biometric data, etc. is sent to the platform 115. Information from the platform 115 can also be transmitted 123 to the monitoring hub 113. Transmission 123 to and from the platform may include encryption and/or compression. Encryption can be used to protect sensitive personal information, and compression can aid in smooth and efficient transmission of the data.

According to various embodiments, the platform 115 includes software that facilitates features such as a parent portal, social interfaces, baby learning platform, and content delivery platform. Although not shown explicitly in FIG. 1, caregiver 109 may be able to directly interact with platform 115, such as through one of these portals or platforms. The platform 115 includes content such as baby profiles, baby de-identified data, learning materials, assessment materials, and baby trends. According to various embodiments, information sent to the platform 115 includes data such as development metrics for individual babies, etc. In addition, the platform 115 performs machine learning on aggregated measurement data, sensor data, and any other development metrics to generate models that predict upcoming behaviors, developments, activities, etc., according to various examples. For instance, measurement data can be used to generate models based on patterns in activity, and these models can be used by particular infant monitoring systems to predict an upcoming activity. Specifically, the patterns in activity can include aspects such as physical activity, emotional signals, sleep patterns, behavior, etc. The upcoming activity can include aspects such as sickness, sleep, mobility, stress, position, comfort, health, vigilance, articulation, receptivity to learning, baby well-being, presence of caregiver, environmental factors, safety of baby, and/or emotional state of baby.

In one example illustrating use of the system shown in FIG. 1, the wearable baby monitoring device 111 provides continuous baby temperature monitoring and the caregiver 109 inputs information about diaper changes. The system detects disturbances in the room, such as with a microphone that provides data to the monitoring hub 113. The wearable baby monitoring device 111 then detects measurement data that is associated with a startle response from baby. The monitoring hub 113 determines that the baby 107 is experiencing too many startling responses. In response, the monitoring hub 113 provides a more soothing environment (e.g. using a projector, music, white noise, etc.) or asks the caregiver to provide a more soothing environment.

In some implementations, the caregiver may also have a wearable device (not shown). The caregiver wearable device can be used to infer when the caregiver 109 is interacting with the baby 107, etc. This information can be used by the monitoring hub 113 and/or platform 115 to assess the effectiveness of certain interactions, etc. In addition, monitoring the locations of the baby 107 and caregiver 109 can be used to alert about a wandering or stolen baby in some applications.

According to various embodiments, the system is used for a single baby or more than one baby. For instance, a system is used to provide instructions for two babies, such as twins or when a caregiver 109 is caring for multiple babies. This allows the caregiver 109 to interact with one monitoring hub 113 and/or mobile device, which can make monitoring multiple babies easier and more efficient. In such implementations, the additional wearable baby monitoring device(s) can also communicate with a monitoring hub 113.

Figure 2A:
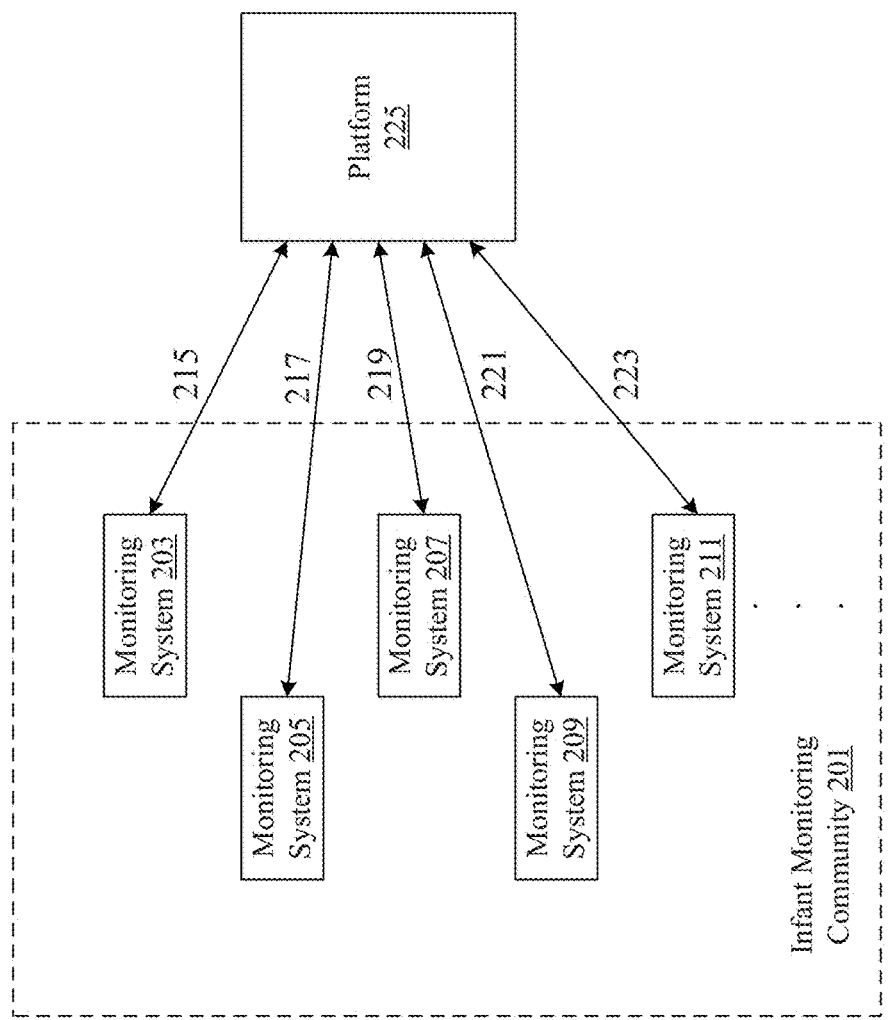
FIG. 2A is a diagrammatic representation of one example of a data aggregation system for gathering information about infants from a community of users monitoring baby activity.

With reference to FIG. 2A, shown is a diagrammatic representation of one example of a data aggregation system for gathering information about infants from a community of users monitoring baby activity. As shown, numerous monitoring systems, such as monitoring system 203, 205, 207, 209, and 211 are part of an infant monitoring community. Any number of monitoring systems can be included, as indicated by the trailing dots in the figure. In some examples, the infant monitoring community 201 includes millions of babies each associated with individual monitoring systems. In these examples, development metrics from these millions of babies can be gathered at the platform 225 such as a remote infant developmental analysis platform. As referred to herein, aggregated measurement data and sensor data includes development metrics such as measurement data from monitoring devices and sensor data from peripheral devices gathered from the infant monitoring community 201. Similarly, aggregated observations, inferences, etc. refer to data aggregated from the infant monitoring community 201.

In the present example, the monitoring systems 203, 205, 207, 209, and 211 are each like the local monitoring system 101 in FIG. 1. As such, each monitoring system 203, 205, 207, 209, and 211 is associated with a different baby. Each of the monitoring systems 203, 205, 207, 209, and 211 can communicate with the platform 225. According to various embodiments, information sent to the platform 225 from the monitoring systems 203, 205, 207, 209, and 211 includes development metrics, and/or any other data gathered by each of the respective monitoring systems. These development metrics (and/or other data) can be used as input to backend machine learning at the platform 225.

According to various embodiments, content such as content libraries and parameterized baby development models can be stored at the platform 225. This content can be shared with the monitoring systems 203, 205, 207, 209, and 211. For instance, information can be sent to a monitoring system 203 in response to a request from the monitoring system 203. In other examples, information can be sent to a monitoring system 205 at a particular developmental time associated with the baby being monitored by monitoring system 205. In yet other examples, information can be sent in response to a receipt of development metrics from a particular monitoring system 207. As described above with regard to FIG. 1, platform 225 includes features such as a parent portal, social interfaces, baby learning platform, and content delivery platform. Each of the monitoring systems 203, 205, 207, 209, and 211 can access these features at the platform 225. In some embodiments, a parent portal can allow a caregiver to directly communicate with the platform 225, such as through a mobile device or computer, without having to communicate through a local monitoring hub. In addition, the platform 225 includes content such as baby profile, baby de-identified data, learning materials, assessment materials, and baby trends, which may also be accessible to monitoring systems 203, 205, 207, 209, and 211 in various embodiments.

According to various embodiments, machine learning can be used to develop models such as development models, health models, kinematic models, and dynamic models at platform 225. These models can be developed using the information gathered from the monitoring systems 203, 205, 207, 209, and 211 from the infant monitoring community 201. Specifically, the gathered data can be used at the platform for research. The gathered data can be used to discover new metrics, develop population statistics, spot trends, etc. For instance, applying unstructured machine learning to the vast amount of gathered measurement data, such as weight, age, gender, location, associated with numerous babies, various predictions can be made and models developed. For example, models can be developed regarding how to impart learning, social interactions, etc. Other examples include discovering trends or markers, such as characteristics that indicate an infant might get sick soon based on its sleep/wake patterns.

Various aspects can be observed and studied at the platform 225 with the help of machine learning. Some examples include wake/sleep prediction, walking detection, detecting quiescent windows, determining when an infant is missing, determining alertness, and predicting an infant's receptivity to learning.

In one example, wake/sleep predictions can be studied at platform 225. Specifically, activity monitoring can be used to identify wake/sleep transitions. Based on a previous week's sleep/wake transitions, a next transition can be predicted. This type of prediction is based on pulse train completion. The time series of wake/sleep is a pulse train that should (for healthy sleep patterns) have regular pulse width and spacing. By estimating those parameters, the onset of the next wake/sleep transition and the duration of the subsequent state (whether waking or sleeping) can be predicted. As an infant grows, the characteristic spacing and width of the pulses will change (eventually converging on a long duration of sleep at night with shorter naps throughout the day for a healthy baby). These changes typically happen on the time scale of months, so sleep predictions may look at time frames on the order of the last week. By observing patterns on this time scale, changes in the sleep patterns can be predicted on a faster time scale than those patterns evolve.

Gathering wake/sleep patterns from a myriad of babies and analyzing this data can help form models of healthy patterns at different developmental levels or ages. Babies typically need different amounts of sleep in different cycles, depending on the baby's age. For instance, a newborn may need about 16-20 hours of sleep per day, a 3-week-old may need about 16-18 hours of sleep per day, a 6-week-old may need about 15-16 hours of sleep per day, a 4-month-old may need about 9-12 hours of sleep per day plus two naps of about 2-3 hours each, a 6-month-old may need about 11 hours of sleep per day plus two naps of about 1.5-2.5 hours each, a 9-month-old may need about 11-12 hours of sleep per day plus two naps of about 1-2 hours each, a 1-year-old may need about 10-11 hours of sleep per day plus two naps of about 1-2 hours each, an 18-month-old may need about 13 hours of sleep per day plus two naps of about 1-2 hours each, and a 2-year-old may need about 11-12 hours of sleep per night plus one nap of about 2 hours long.

Various factors can be used to predict sleep schedules, such as Galvanic Skin Response (GSR) activity (i.e. arousal), last known sleep cycle, audio detected by a sensor, etc. In some examples, models are created for predicting predict sleep schedules based on an infant's data and/or aggregated data from numerous babies. According to various embodiments, the sensors include mechanisms for determining whether the baby is prone or supine or in some other position. Sensors may include accelerometer, magnetic sensors, gyroscopes, motion sensors, step counters, rotation vector sensor, gravity sensor, orientation sensor, and linear acceleration sensor. According to various embodiments, it is recognized that is particularly useful in the infant context to determine infant position, such as whether the infant is resting supine, prone, sitting, etc.

A wearable casing for the sensors may be worn by an infant in a particular manner such that directionality is known. For example, the wearable casing may be an anklet, bracelet, sock, shoe, diaper, or included in a onesie. An indicator may be included on the wearable directing a caregiver on the appropriate positioning or directionality of the wearable. In addition, observations can be made about the baby's sleep patterns and sleep state, and the baby's level of fatigue can be estimated in some examples. For instance, if the sleep schedule for the baby indicates that the baby is normally asleep at this time but is not currently asleep, then a guess can be made that the baby is probably fatigued. Specifically, if the baby is usually napping at this time and is currently awake, a guess can be made that the baby may be irritable. In some applications, suggestions can be made to the caregiver regarding providing a calm environment for the baby to promote sleep, avoiding stimulation or teaching, etc. According to various embodiments, models developed at the platform 225 can also be used to predict development for a particular baby when the particular baby is compared to these models.

In another example, detection of walking can be studied at platform 225. Specifically, activity data from the infant monitoring community 201 can be used to determine when an infant is walking or moving in various ways. For instance, pre-walking may include smooth accelerations, whereas walking may include sharp spikes in acceleration associated with foot falls at reasonable periods. Also, joint angles and bone positions with respect to models that include torso bounce and ground reaction force can also indicate whether an infant is walking or moving in some other way. By analyzing data about baby movements, models can be predicted regarding walking detection. In some examples, the measurement data associated with an infant can be combined with information provided by a caregiver about when the baby walked, etc. Comparing a particular baby's walking to models can help predict the baby's developmental age, etc. Mechanisms for developing models relating to walking, etc. can also be applied to data sets outside the infant category. For instance, this system could also be used with physical therapy patients of all ages.

In another example, mechanisms can be used at platform 225 to determine "quiescent windows," when an infant is inactive, quiet, and still. Developing models predicting these "quiescent windows" and using them at the monitoring systems can lift health and hygiene of the babies, such as by increased use of diapers.

In yet another example, a missing baby can be detected based on models developed at platform 225. Predictions can be made about when the baby is moving not under its own power. For instance, patterns of movement or location can be studied to determine when an anomaly is detected. In some examples, geolocation can be included to indicate when baby is traveling with someone other than an authorized caregiver. In some applications, a caregiver can be notified to check on the baby and confirm the baby's whereabouts. This can be particularly helpful in keeping babies safe not only from abductions, but also if the baby is inadvertently left in a car or other location. Furthermore, this technology could be used with older children to determine if they have wandered off, etc.

In another example, alertness of an infant can be studied at platform 225. Specifically, measurement data can be studied to detect when an infant is alone and alert, and the length of time the baby has been alone and alert. Detecting when an infant is alone can be based on factors such as background audio analysis, but is complicated by situations where the infant is not actually alone, but is just being ignored. Input from caregivers can also be included. Models can be used to predict when babies might benefit from interaction or learning experiences.

In another example, receptivity to learning can be studied at platform 225. Determining appropriate windows of time for an infant's receptivity to learning can help caregivers know when to present teaching materials or interaction in a more productive manner. In order to determine these appropriate windows, numerous factors can be considered. Specifically, data such as sleep/wake cycles, vocalization, temperature, age, gender, weight, and other biometric measures collected from infant monitoring community 201 can be considered. Additionally, data from one or more of an intentionality detector, gaze detector, shared attention detector, and cognition detector can be used to determine an infant's receptivity to learning. Furthermore, data about an infant's environment, such as audio levels, time of day, location, ethnicity, etc. can also be considered. Additional data from one or more caregivers, such as diaper changes, self-reporting, and lesson feedback can also be considered. This data can be analyzed to help determine when an infant is most receptive to learning and what type of material is appropriate to present at a particular time. Models can be created that indicate windows of receptivity to learning and the appropriate teaching/learning materials. These models can be used at individual monitoring systems for application to individual babies. For instance, the absence or presence of specific stimulation, as indicated by the system or from caregiver input, such as auditory, sensory, tactile, etc. can be used to select an age-weighted, progress-weighted learning program from a model developed at the platform 225. Specifically, knowing the age of the baby can help determine whether physical, cognitive, or language learning materials should be presented. For example, babies between about 0-3 months may be receptive to learning gross motor skills, babies between about 3-9 months may be receptive to learning gross motor skills and language, babies between about 9-18 months may be receptive to learning fine motor, language and social skills, and babies between about 18-24 months may be receptive to learning fine motor, language, social, and discrimination skills. At certain ages, there may be a hierarchy of learning, wherein the baby is receptive to multiple skills, but that these skills can be presented in a hierarchy based on the baby's developmental level. According to various embodiments, a particular baby monitoring system can predict windows of receptivity when an infant is receptive to learning. In these embodiments, the baby monitoring system processes measurement data and selects and customizes learning materials appropriate for the infant. The learning materials can be customized based on factors such as the baby's developmental age, readiness, previous learning experiences, caregiver feedback, etc.

Figure 2B:
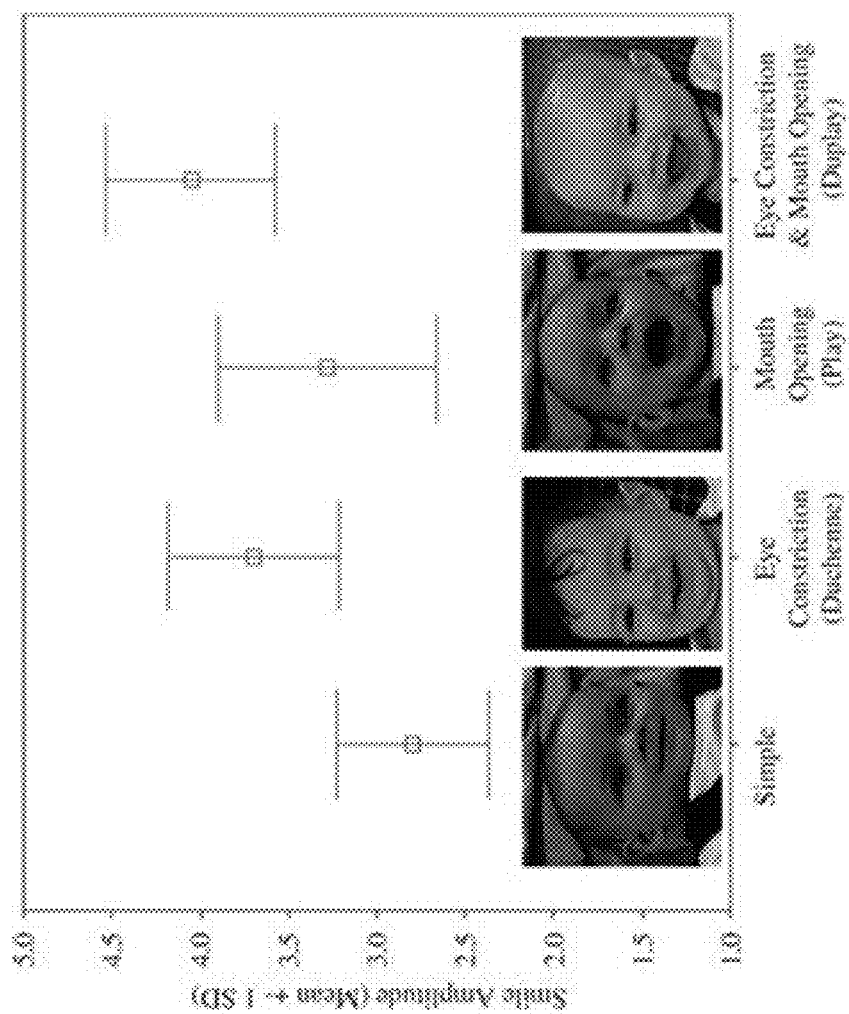
FIG. 2B is an example chart showing smile intensity that may contribute to the meaning of smiles.

Various features can be used to assess an infant's receptivity, such as an intentionality detector, gaze detector, shared attention detector, and cognition detector. In one example, an emotional intensity hypothesis can be used to determine an infant's receptivity to learning. In particular, an infant's smile amplitude can be measured based on data from a camera or other input device in a monitoring system, and the baby's receptivity can be correlated. With reference to FIG. 2B, shown is a graph illustrating various smile amplitude versus various facial expressions. These facial expressions can indicate the amount of enjoyment an infant is experiencing at a given time. The information in this chart can be used along with data from an infant monitoring system such as a camera feed, audio levels, etc. to determine when an infant is in a good state to learn. In the graph shown in FIG. 2B, approach and withdrawal indexed by patterns of gazing and movement during games contribute to the meaning of smiles (Fogel et al., 2000). For example, during peekaboo games, infants tend to gaze at the parent during all types of smiles, suggesting approach-oriented visual attention. During the climax of tickle games, by contrast, infants engaging in open-mouth smiles with eye constriction show mixed patterns of both gazing at and away from parents. Such patterns may correspond to feelings of enjoyment of active participation in a highly arousing situation and enjoyment of escape. These findings suggest that the same smiling actions can reflect different positive emotions depending on co-occurring infant action and the dynamics of social process.

According to various embodiments, the coordination of smiles with gazing changes and becomes more precisely patterned with age. Simulation studies suggest that, at 3 months, the pattern of gazing away during a smile actually occurs less than expected by chance. The simulation studies indicate that 3-month-olds tend to begin and end their smiles within the course of a gaze at the parent's face. That is, early expressions of positive emotion are dependent on continuous visual contact with the parent. By 6 months, infants redirect their attention after sharing positive emotional expressions with their parents. They tend to gaze at mother's face, smile, gaze away, and then end the smile. Such gaze aversions—at least among 5-month-olds playing peekaboo—tend to occur during higher intensity smiles and smiles of longer durations. Accordingly, information gathered about an infant's smiles and gaze can also help to determine an infant's age, etc. In turn, this can help determine what type of learning materials or activities should be presented to the baby during a window of receptivity.

According to various embodiments, analysis at platform 225 is an ongoing process. Various observations, patterns, models, can continually be discovered, refined, etc. Consequently, these models can change over time based on the input from the infant monitoring community 201. In some examples, expert models can initially be used and replaced with continually refined models.

Figure 3:
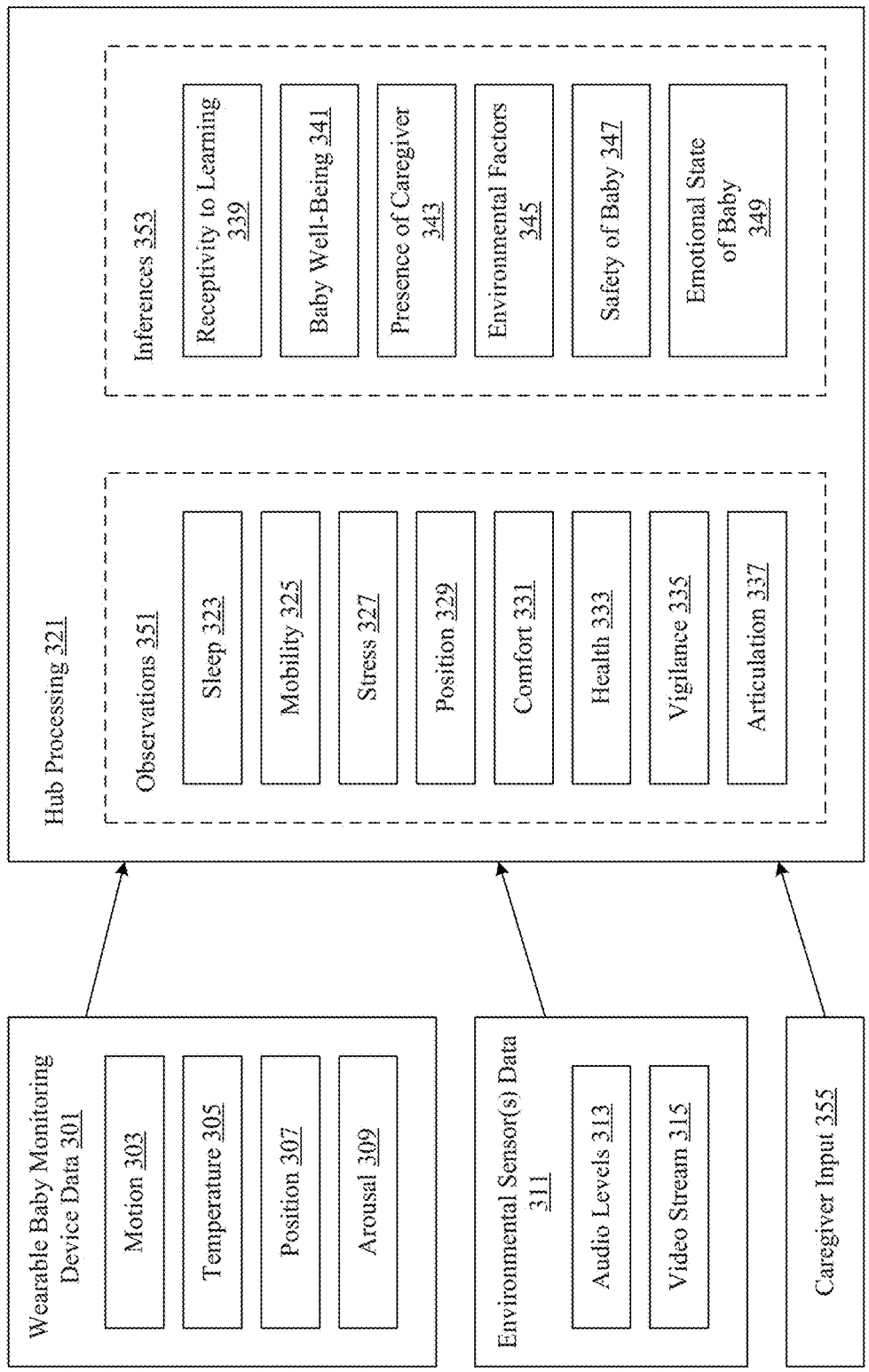
FIG. 3 is a diagrammatic representation of one example of an infant monitoring data aggregation and processing system.

With reference to FIG. 3, shown is a diagrammatic representation of one example of an infant monitoring data aggregation and processing system. This system includes an infant monitoring device, environmental sensor(s), and a monitoring hub. Measurement data is gathered by the wearable baby monitoring device and environmental sensors and sent to the monitoring hub for processing. As shown in the diagram, wearable baby monitoring device data 301 gathered by the baby monitoring device includes motion 303 (i.e., activity), temperature 305, position 307, and arousal 309. In some examples, the position 307 can include a geoposition of the baby. Environmental sensor(s) data 311 gathered from devices such as microphones or cameras includes audio levels 313 and video stream 315. However, in some examples, the environmental sensors can be omitted, such as when a simplified system is employed. For instance, if the system is used during an outing, cameras, peripheral devices, etc. may be disconnected and only input from the wearable baby monitoring device may be used.

In the present example, the monitoring hub receives data from the wearable baby monitoring device and the environmental sensor(s). According to various embodiments, the data is collected continuously around the clock. In some examples, this may mean periodic but consistent monitoring, such as at designated intervals of time. Hub processing 321 can be applied to the data received to yield various observations 351 and inferences 353. Some of the observations 351 that can be made at the monitoring hub based on data measurements include sleep 323, mobility 325, stress 327, position 329, comfort 331, health 333, vigilance (e.g. baby attention, cognitive responsiveness) 335, and articulation (i.e., speech articulation) 337. Some of the inferences 353 that can be made at the monitoring hub based on measurement data include receptivity to learning 339, baby well-being 341, presence of caregiver 343, environmental factors 345, safety of the baby 347, and emotional state of the baby 349. Although observations 351 and inferences 353 are shown as different categories, various items can be categorized in either set without deviating from the scope of this example.

Numerous combinations of measurement data from the wearable baby monitoring device and/or the environmental sensor(s) can be used to make observations or inferences. According to various embodiments, data is first collected about the baby, the data is scaled, and then a model or prediction is applied to the baby. Specifically, aggregated data can be collected at the platform, as described above with regard to FIG. 2, and models, predictions, etc. can be developed. These models, etc. can then be accessed from the platform by individual monitoring hubs. A particular baby monitoring system can then perform hub processing 321 that can use these models, etc. to analyze measurement data for a particular baby.

Observations and/or inferences can be made for a particular baby and made available to a caregiver. This information can help the caregiver better care for the baby. In some examples, the information can be used to provide guidance or advice to caregiver, such as through the monitoring hub and/or mobile device. For instance, hub processing 321 may determine that the baby is currently in a particular position 329 (also referred to as orientation) that may correlate with a breathing problem (associated with SIDS, etc.) or non-preferred/unsafe position. This observation 351 can lead to a notification to the caregiver about this finding. In some examples, the notification can also include recommendations about how to reposition the baby, etc. In another example, the baby's growth can be monitored, such as by caregiver input 355, or by a sensor such as a scale (not shown) that is connected to the system as a peripheral device. This growth can be used to estimate the baby's developmental age and from this information a schedule can be developed at the hub outlining when an infant should be taught something. In yet other examples, motion 303, such as a shake of the baby's hand can be monitored to determine motor development, blood flow can be monitored and correlated to brain development, and electrodermal activity can be monitored to predict health 333 occurrences such as epileptic seizures. In another example, predictions about the baby's activity can be made using data from the accelerometer and GSR, as described in more detail with regard to FIG. 4. Based on this data, a prediction can be made about whether the baby is awake/asleep, eating, crawling/walking/running, etc. Various inputs can be monitored to yield observations and predictions about the baby.

Various observations 351 can be made about the baby based on measurement data associated with the baby. For instance, sleep 323 observations can be used to predict the upcoming sleep patterns of the baby, and can alert the caregiver if sleep patterns are disturbed. For instance, if the sleep patterns are disturbed, this may indicate that the baby is getting sick, etc. Observations about mobility 325 can help determine how the baby is moving relative to its developmental age and can be used to advise the caregiver about how to teach or help the baby at a developmentally appropriate level. Observations about stress 327 can help determine if there are conditions that could be changed to reduce the baby's stress. As mentioned above, position 329 can be observed to see if a current position is associated with a non-favored or unsafe position and the caregiver can be notified. Position 329 can also refer to the baby's orientation, such as whether the baby is lying down, standing up, crawling, walking, etc. Furthermore, the baby's orientation can include whether the baby is prone or supine. These observations can be made based on data such as motion 303 and position 307. Observations about comfort 331 can be made and findings can be provided. Observations about health 333 can also be made, such as whether the baby's temperature constitutes a fever, etc. Observations about vigilance 335 includes whether an infant is alert and awake, etc. In addition, observations about articulation 337 may include detecting speech articulation using environmental sensor data 311 such as audio input. Although particular examples of observations are shown and described, it should be recognized that additional observations can also be made within the scope of this disclosure. Likewise any combination of observations (such as a limited set of those shown) can be used depending on the desired operation of the system.

Various inferences 353 can be made about the baby based on measurement data associated with the baby. For instance, inferences about the baby's receptivity to learning 339 can be made. As described above with regard to FIG. 2, various factors can be used to assess receptivity to learning 339 such as developmental age. These inferences can be used to determine when and/or what the baby should be learning. Providing appropriate learning materials (such as advice to the caregiver about what to teach or how to interact with the baby) at the appropriate time can help with the baby's brain development. Inferences about the baby's well-being 341 can be made in some examples. For instance, considering factors such as the health and emotional state of the baby can indicate the baby's overall well-being. In some examples, these inferences can help to determine how effective a particular caregiver is meeting the baby's needs, etc. Inferences about the presence of a caregiver 343 can also be made. For instance, measurement data from the baby monitoring device and/or a caregiver device can indicate whether the caregiver is present at a particular time. Inferences about environmental factors 345 can also be made. For instance, environmental sensor data 311, such as audio levels 313, can be used to assess what is good for the baby versus what is not good for the baby. In some examples, the system can use a predictive model to identify if an environment is cognitively good for an infant, using factors such as visual clutter, sound pollution, light over-intensity, not enough interaction, etc. Specifically an environmental suitability model can be used that reflects a relationship between a range of environmental conditions and expected infant characteristics corresponding to these environmental conditions. For example, visual clutter may be associated with a higher degree of stress, sound pollution may be associated with less (or lower quality) sleep, etc. Additionally, inferences can be made about safety of the baby 347. In some examples, safety may include the baby's position (e.g. "back to sleep"), and other physical safety features. In other examples, safety may include whether the baby is "missing," such as if the baby has wandered off, fallen, or been taken by an unauthorized caregiver. Inferences about the emotional state of the baby 349 can also be made, such as whether the baby is stressed, etc. In some examples, these inferences can help to determine how effective a particular caregiver or interaction is for placating the baby's stress. In other examples, these inferences can be used to determine what types of activities, environments, schedules, etc. best suit this particular baby. Although particular examples of inferences are shown and described, it should be recognized that additional inferences can also be made within the scope of this disclosure. Likewise any combination of inferences (such as a limited set of those shown) can be used depending on the desired operation of the system.

Figure 4:
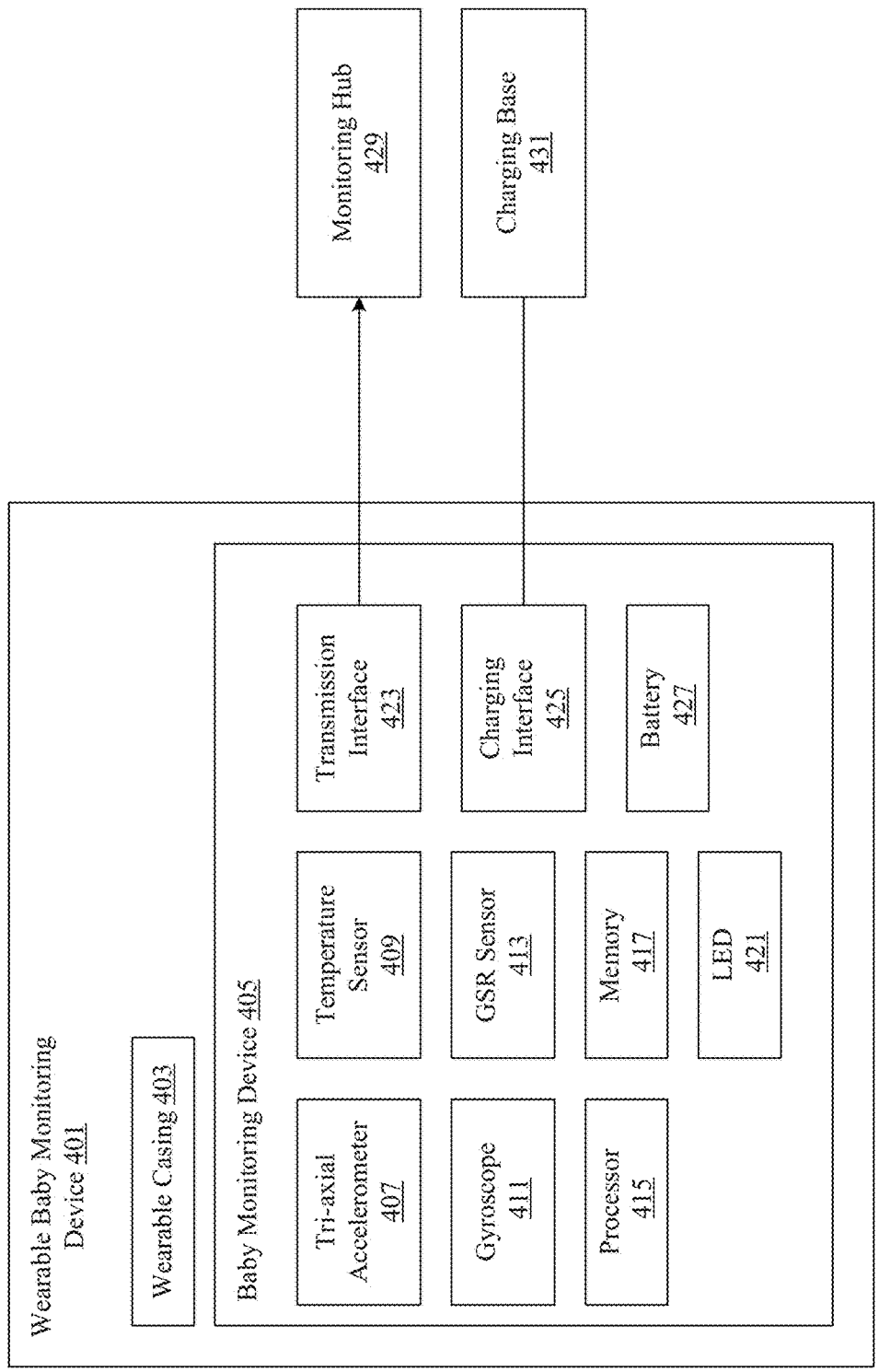
FIG. 4 is a diagrammatic representation of one example of a wearable baby monitoring device.

With reference to FIG. 4, shown is a diagrammatic representation of one example of a wearable baby monitoring device. The wearable baby monitoring device 401 is an infant-friendly wearable device, which monitors baby activity and other baby related biometric measures. As shown in the present example, the wearable baby monitoring device 401 includes a wearable casing 403 and an infant monitoring device 405. According to various embodiments, the baby monitoring device 405 is detachable from a wearable casing 403, examples of which are described with regard to FIGS. 5A-5C.

In one embodiment, the wearable baby monitoring device 401 allows the baby monitoring device 405 to be worn on the ankle of an infant. The baby monitoring device collects activity and emotional state data. In the present example, this data is collected continuously around the clock. Specifically, baby monitoring device 405 collects data and provides notifications. In various examples, the baby monitoring device 405 can be used for data logging. According to various embodiments, the device is expected to store data from multiple sensors and also do moderate processing of the data from the sensors. This processing may include filtering, dimensionality reduction and cleanup of the raw data. Because the device is also intended for use as an infant monitor, low-latency processing of some sensors e.g. position may be required. However, in some instances, the baby monitoring device 405 may not store content. By including less content and/or other features, the baby monitoring device 405 can be designed with a smaller size to allow for a more comfortable experience for the baby. In addition, including fewer features can also reduce complexity of the device, and thereby reduce possible malfunctions, etc.

In the present example, baby monitoring device 405 includes various components, such as tri-axial accelerometer 407, temperature sensor 409, gyroscope 411, galvanic skin response (GSR) sensor 413, processor 415, memory 417, light emitting diode (LED) 421, transmission interface 423, charging interface 425 and battery 427. The tri-axial accelerometer 407 measures an infant's activity, such as movements registering more than about 50 Hz in some examples. The accelerometer data is used to measure the baby's movement. The temperature sensor 409 measures the baby's body temperature. According to various examples, the baby's body temperature is continuously monitored. The gyroscope 411 measures the baby's orientation. The GSR Sensor 413 measures galvanic skin resistance (GSR). For instance, the GSR sensor 413 can measure the amount of sweat or moisture detected on the body. The GSR is a low latency arousal measurement, and can be used to measure the baby's stress levels.

In the present example, the processor 415 can be an ARM Cortex M0-M3, or the like, depending on the application. In some examples, the processor 415 can have limited or no digital signal processing (DSP). The memory 417 can be of any size, depending on the application. In some examples, the memory 417 can have a size of 384 kb. The transmission interface 423 can be used to communicate with a monitoring hub 429. Specifically, measurement data can be sent from the baby monitoring device to monitoring hub 429. According to various examples, transmission interface 423 can use a transmission protocol such as Bluetooth LE (BLE 4.0), although any suitable protocol can be used.

In the present embodiment, the baby monitoring device 405 includes an LED 421 that can communicate status information to a caregiver. For instance, the LED 421 can indicate that the device is charging when the LED is illuminated. In some examples, the LED can be a single neo-pixel LED.

According to various embodiments, battery 427 stores charge for operation of the baby monitoring device. One type of battery that can be used is a Li—Po battery (110 mAh), which is adequate for a day's operation. However, any type of battery can be used, depending on the application and desired use. In some examples, the battery can be recharged via a charging interface 425 that can be periodically placed in contact with a charging base 431. For instance, the device can be charged using contact and/or wireless inductive charging. If the battery life can be expected to last at least 24 hours in the present example, then the device can be charged once per day. The battery 427 and/or charging interface 425 includes a charge circuit in some instances.

According to various embodiments, the wearable baby monitoring device must be safe, secure and easy to use. In the present example, the baby monitoring device 405 is waterproof and hypoallergenic. In addition, the wearable baby monitoring device contains no serviceable parts and the electronic components are completely sealed in this example.

In some examples, the target demographic for the baby is between about 0-24 months of age. Of course, this age range can be expanded or contracted depending on the particular application or needs being addressed. In addition, although the wearable baby monitor device may be used primarily indoors in some applications, the baby monitoring device can also be used outdoors according to various embodiments. For instance, the baby monitoring device can be used during an outing or trip. If the baby monitoring system includes one or more peripheral devices such as a camera, microphone, etc. that is located in a stationary position like the baby's room, certain features may not be available when the device is used outdoors. However, continuous monitoring of the baby can continue for measurements such as temperature, activity, GSR, position, etc. remotely in some examples.

Figure 5A:
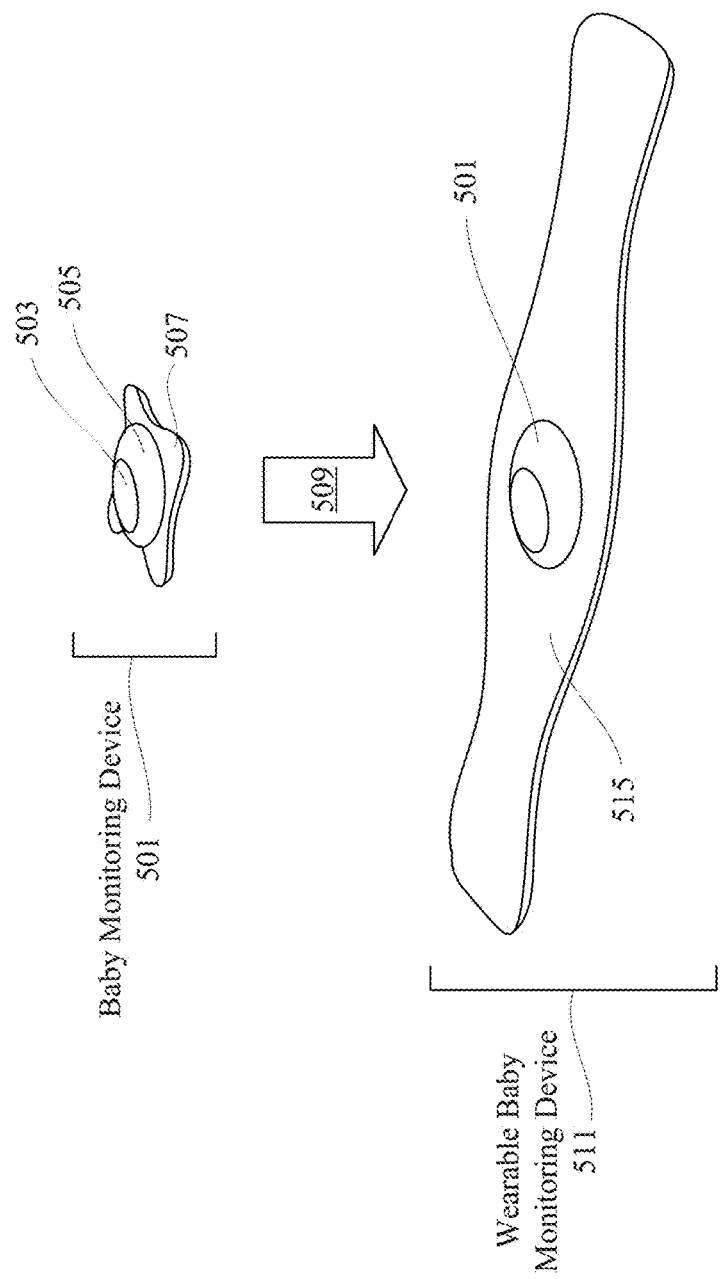
FIG. 5A is a diagrammatic representation of one example of an infant monitoring device and a wearable baby monitoring device.
Figure 5C:
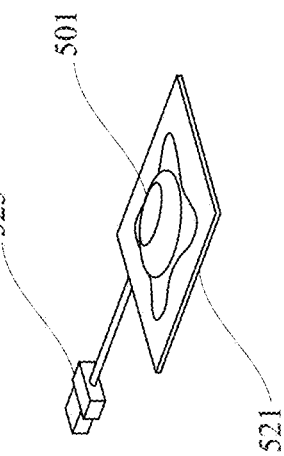
FIG. 5C is a diagrammatic representation of another example of an infant monitoring device docked on a charging base.
Figure 5B:
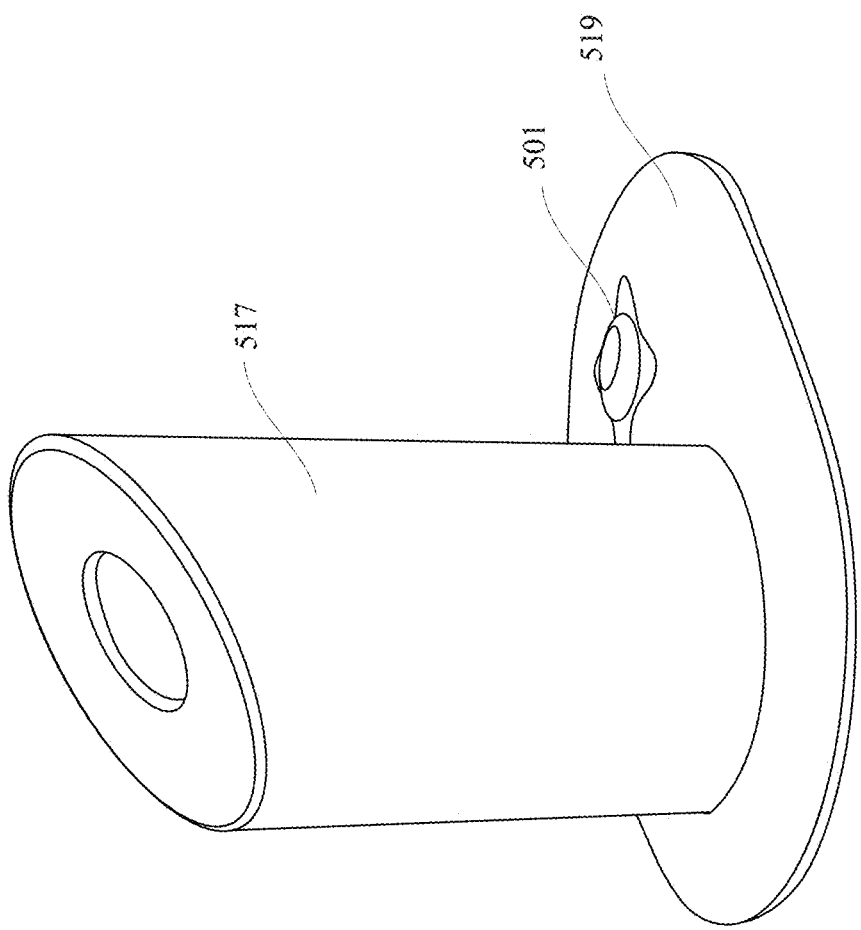
FIG. 5B is a diagrammatic representation of one example of an infant monitoring device docked on a charging base.

FIGS. 5A-5C illustrate examples of baby monitoring devices being used in different contexts. With reference to FIG. 5A, shown is a diagrammatic representation of one example of an infant monitoring device and a wearable baby monitoring device. In particular, baby monitoring device 501 is shown with a base 507, body 505 and LED window 503. When the baby monitoring device 501 is engaged 509 with wearable casing 515 the wearable baby monitoring device 511 is ready to wear by an infant. For instance, the wearable baby monitoring device can be worn around the ankle of an infant and the ends can be secured, such as by a snap or other closure. In some examples, the baby monitoring device 501 can be engaged with the wearable casing 515 through a snug fit, wherein the body 505 overlaps one side of the wearable casing 515 and the base overlaps the other side. In such examples, the body 505 and base 507 may be connected with a rod that has a smaller cross-section than that of the body 505 or base 507. Furthermore, in these examples, the wearable casing can be made of an elastic material that allows some stretching to fit and secure the baby monitoring device 501. In other examples, the base 507 may slip into a pocket or sleeve located in the wearable casing 515.

Although a particular example of an infant monitoring device 501 and wearable casing 515 are shown, various designs and configurations are possible within the scope of this disclosure. Specifically, baby monitoring device can be made in any of a variety of shapes. For instance, the body can be square instead of circular, the base can be circular instead of square, etc. Furthermore, the wearable casing 515 can be made in various shapes and designs. For instance, the wearable casing can alternatively be designed as a continuous loop that may or may not be adjustable in diameter. In other examples, different fastening devices can be used to secure the ends of a wearable casing 515 such as a buckle (wristwatch style), mating sides that snap together, etc.

With reference to FIG. 5B, shown is a diagrammatic representation of one example of an infant monitoring device docked on a charging base. As shown, the charging base is part of an infant station. According to various embodiments, an infant station includes various features such as a charging station (shown in the present example with an infant monitoring device 501 docked to it), peripheral devices, etc. The peripheral devices includes components such as a projector 517, camera, microphone, speaker, screen, input device, etc. In some examples, the baby station includes software that allows data pre-processing, ambient sensing, content cache, and baby status assessment. Furthermore, the baby station includes content such as learning content and schedule(s), in some instances. In addition, the baby station can operate as a monitoring hub in some examples.

In the present example, the charging station can be induction-based. The projector 517 may be used to display lights or images in an infant's room, etc. Although not shown, the baby station may include a power cord that can be plugged into an outlet, or the like, which can provide power for the various components of the baby station. In some examples, the peripheral device(s) can be removable from the baby station.

With reference to FIG. 5C, shown is a diagrammatic representation of another example of an infant monitoring device docked on a charging base. In particular, the charging base 521 includes a plug 523 that can be used to provide charge via a USB port, micro USB port, etc. As shown, an infant monitoring device 501 is docked on the base 521. In the present embodiment, the charging base is induction-based. However, alternative connections can be implemented within the scope of this disclosure. This type of charging base may be convenient if the baby monitoring device 501 is used remotely such as during travel or an outing, especially if a mobile device is used by a caregiver to view monitoring information. The charging base can be used with the mobile device to charge the baby monitoring device 523 on-the-go because the charging base is small and easy to pack, store, and use.

Figure 6:
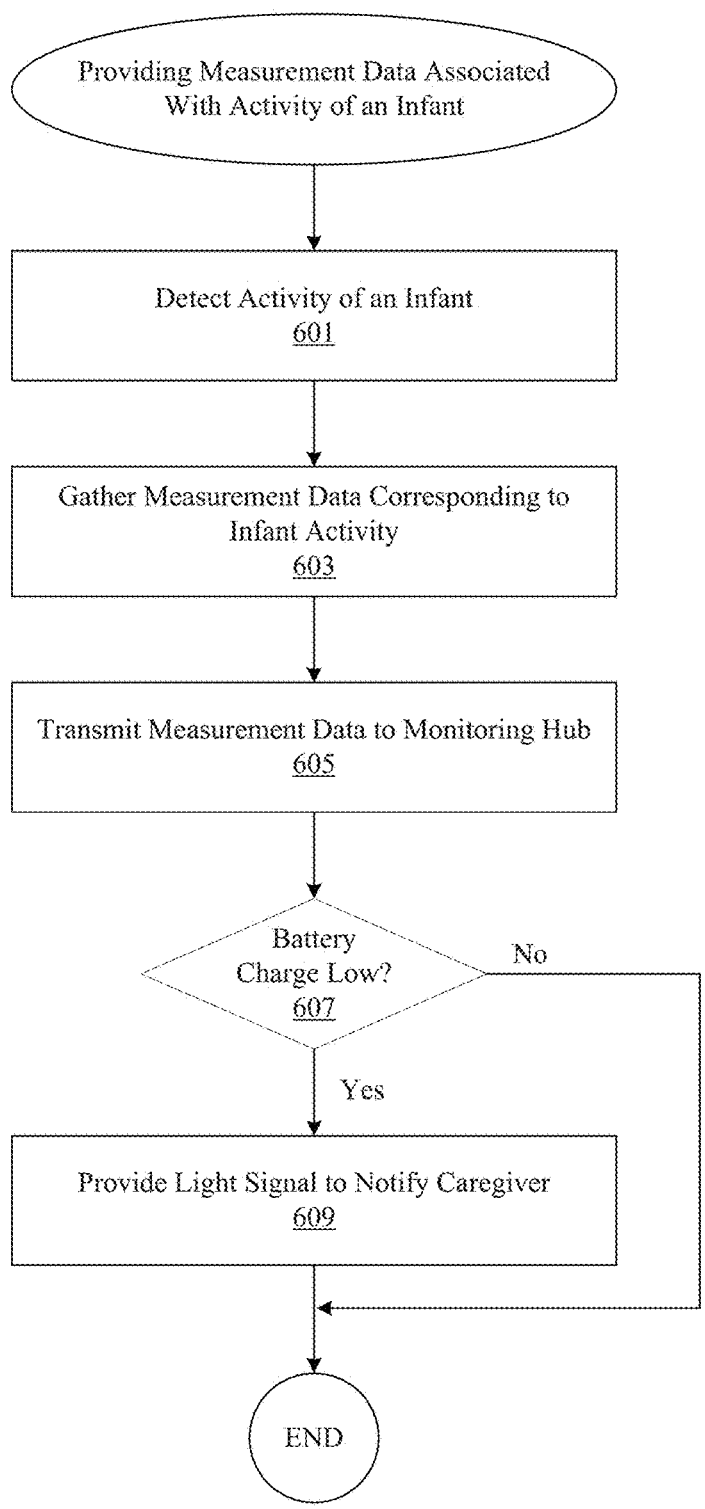
FIG. 6 is a flow diagram of one example of a process for providing measurement data associated with activity of an infant.

FIG. 6 is a flow diagram of one example of a process for providing measurement data associated with activity of an infant. In the present example, activity of an infant is detected at 601. This activity is detected by an infant monitoring device, as described above with regard to various embodiments. Detection may be based on a change in measurements, such as movement or a temperature change, in some examples. Alternatively, detection may correspond to periodically detecting activity based on a schedule, set times, etc. The baby monitoring device then gathers measurement data corresponding to the activity at 603. This measurement data includes information such as motion (i.e., activity), temperature, position, and arousal, as also described above with regard to various embodiments. The measurement data is then transmitted to a monitoring hub at 605. As described above, the monitoring hub can then process the data and provide information about the baby's activity to a caregiver. According to various embodiments, the monitoring hub can also provide this data to the platform for further analysis.

In the present embodiment, the baby monitoring device can also include a check to make sure its battery is sufficiently charged at 607. If the battery charge is low, a light signal can be illuminated to notify the caregiver 609 to charge the baby monitoring device. For instance, an LED located on the baby monitoring device can be illuminated. Alternatively or additionally, a notification can be sent to the caregiver via the monitoring hub and/or a mobile device to charge the baby monitoring device. If the battery charge is not found to be low, no notification is provided. As shown in the present embodiment, this battery charge check is performed after measurement data is provided. By including the battery check as part of this process, the battery is checked often. However, it should be recognized that the battery check at 607 and notification 609 can be omitted from this process in some examples, and the battery check can be performed at other times, such as at periodic intervals or set times.

Figure 7A:
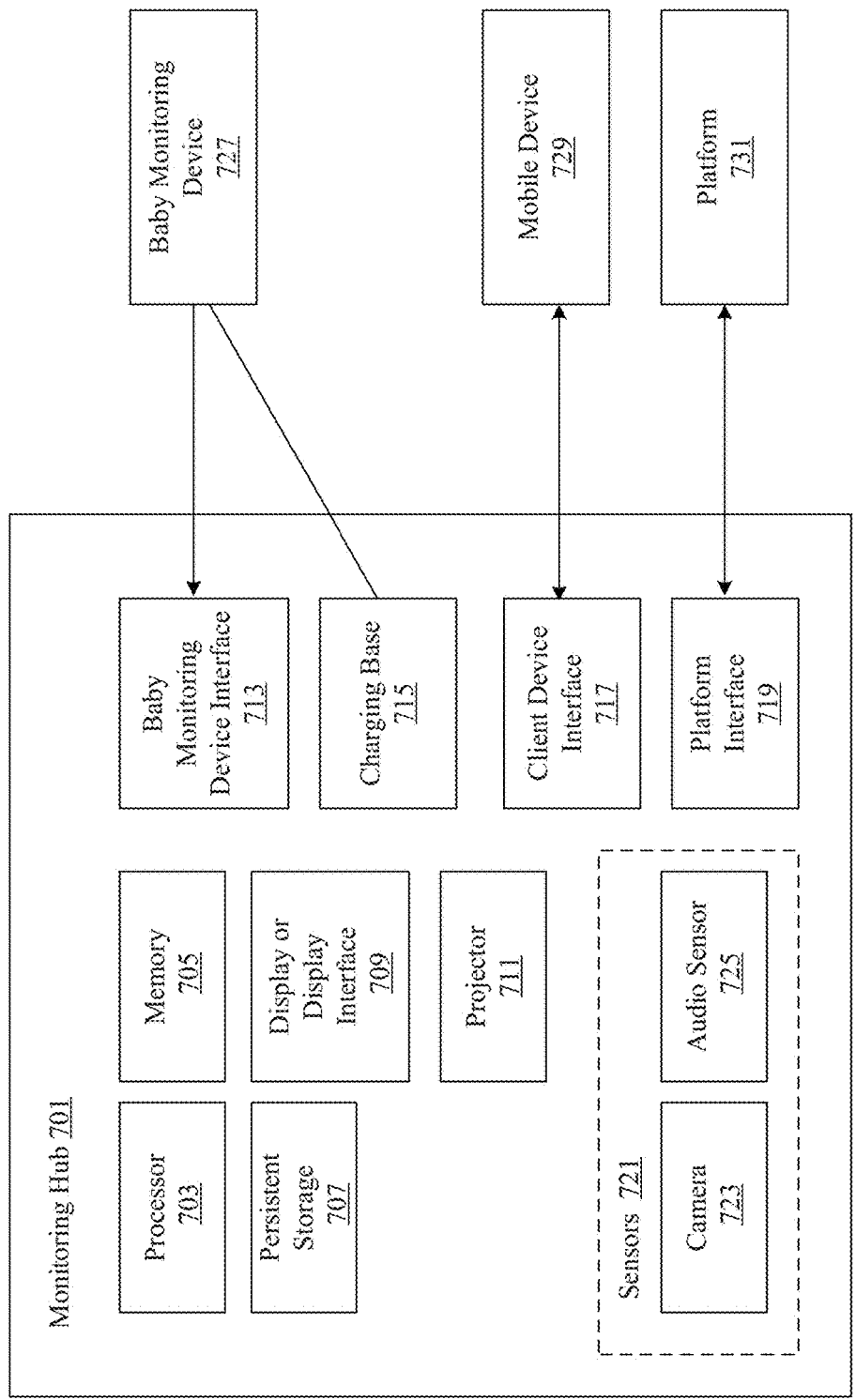
FIG. 7A is a diagrammatic representation of one example of a monitoring hub.
Figure 7B:
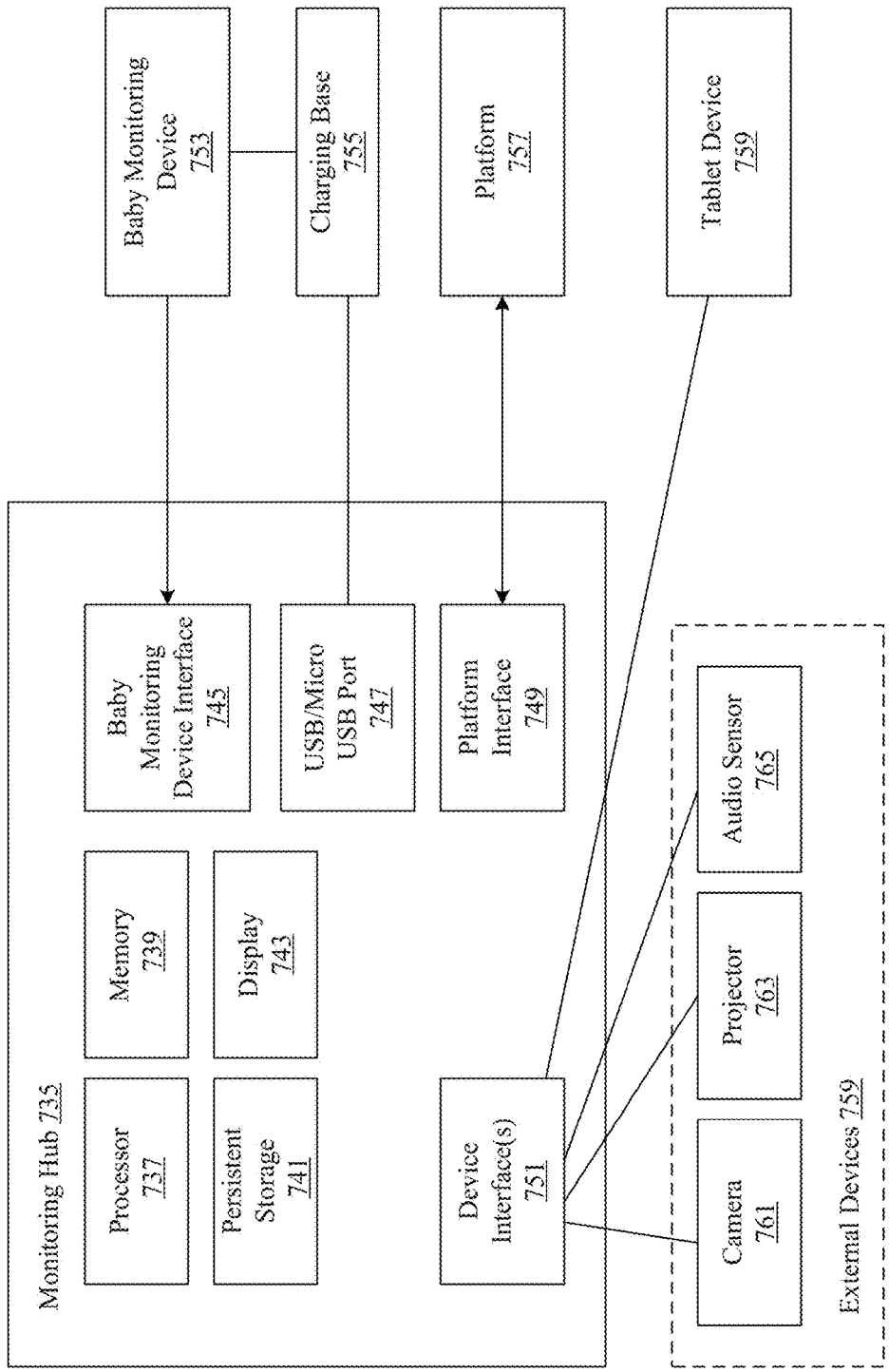
FIG. 7B is a diagrammatic representation of another example of a monitoring hub.

FIGS. 7A-7B illustrate examples of monitoring hubs. Various configurations can be used for a monitoring hub within the scope of this disclosure. With reference to FIG. 7A is shown one example of a monitoring hub. As described above with regard to various examples, a monitoring hub 701 can receive measurement data from an infant monitoring device 727 and can process this measurement data at the monitoring hub 701.

According to various embodiments, monitoring hub 701 can provide data pre-processing, ambient sensing (local sensing of environment, vibration sensing, audio sensors, cameras), content cache, and/or baby status assessment. The monitoring hub 701 can also include learning content and schedule(s). In addition, the monitoring hub can provide digital signal processing, a human interface, and data security. Furthermore, model-based content adaptation can be provided at the monitoring hub 701. Accordingly, models and library content obtained from the platform 731 such as a remote infant developmental analysis platform can be tailored for the baby's developmental age and needs. Specifically, development models can be evaluated at the monitoring hub 701 and content from the library can be selected and customized. One example of content adaptation as applied to interactive activities includes selecting a sequence of interactive activities that is developmentally appropriate and doesn't exhaust the baby. In particular, a determination can be made about a particular baby's developmental age and the duration of an interaction window appropriate for this age. Using this information, content from the content library stored at the platform 731 can be selected and adapted to be appropriate for the baby. This adapted content can then be presented to the baby during an appropriate interaction window.

In the present example, the monitoring hub 701 includes a processor 703, memory 705, persistent storage 707, display or display interface 709, projector 711, sensors 721 (including camera 723 and audio sensor 725), baby monitoring device interface 713, charging base 715, client device interface 717, and platform interface 719. Although particular components are shown, it should be recognized that some of these components can be omitted without deviating from the scope of this disclosure. For instance, the projector 711 could be removed. Additional components can also be included depending on the desired operation of the monitoring hub 701.

According to various embodiments, the monitoring hub 701 can act as an infant station, such as that described with regard to FIG. 5B. In these embodiments, the baby station includes software that allows data pre-processing, ambient sensing, content cache, and baby status assessment. Content that can be included includes learning content and schedule(s).

In the present embodiment, processor 703 and memory 705 can be used to process data measurements received from baby monitoring device 727. Specifically, this data can be processed to develop observations and/or inferences as described above with regard to FIG. 3. In addition, processor 703 and memory 705 can be used to customize content for the baby such as learning materials to be age appropriate. Persistent storage 707 can store content and schedule(s), as well as any models, charts, etc. received from the platform 731. Furthermore, persistent storage 707 can store information specific to the baby.

In the present example, display or display interface 709 allows a caregiver to view and/or interact with the monitoring hub 701. For instance, notifications, alerts, suggestions, etc. can be displayed for the caregiver through the display or display interface 709. In some instances, the display may be a screen or monitor. In addition, an input device, such as a keyboard may be included, especially if the display is not touch sensitive. In other instances, a display interface may include a port that allows a monitor to be connected as a peripheral device. In addition, the monitoring hub 701 can be connected to a computer such as a laptop, desktop, etc.

In some examples, a projector 711 can be included as part of the monitoring hub 701. For instance, a projector 711 can be included as part of an infant station and can be used to display lights or images for the baby to see. This feature can be useful to augment the environment with soothing lights, colors, or images. In some examples, this may be used to present learning content to the baby.

In the present example, sensors 721 include camera 723 and audio sensor 725. Camera 723 can be used to transmit video for a caregiver to see on a monitor, such as through a mobile device 729. Camera 723 can also be used to gather data measurements associated with the baby such as position. Audio sensor 725 can be used to transmit audio for a caregiver to hear, such as through a mobile device 729. Audio sensor 725 can also be used to gather data measurements associated with the baby's surroundings and environment. In addition, the audio sensor 725 can be used to gather data measurements about sounds from the baby, such as cries, verbal articulation, etc. In some examples, the sensors 721 can be removable from the monitoring hub 701, especially to allow better positioning of these devices relative to the baby. Other components of the monitoring hub 701 may be removable as well, such that the monitoring hub 701 has a modular style.

In the present embodiment, baby monitoring device interface 713 facilitates wireless communication with the baby monitoring device 727. In addition, the baby monitoring device 727 can be charged at a charging base 715 associated with the monitoring hub 701. The charging base 715 can be induction-based, such that the baby monitoring device 727 can be placed in contact with the charging base 715 during charging. One example of a charging base included in an infant station is described above with regard to FIG. 5B.

According to various embodiments, monitoring hub 701 includes a client device interface 717 that allows the monitoring hub 701 to communicate wirelessly with a mobile device 729, such as a smart phone, tablet, or the like. A mobile device 729 includes software that facilitates features such as data pre-processing, early warning, and remote observation. In addition, content that can be included on the mobile device 729 includes learning, social, and environmental information. The caregiver is the typical user of the mobile device 729, and can view various data from the baby monitoring device 727. In some instances, raw data measurements from the baby monitoring device may be viewed. However, processed information from the monitoring hub 701 may provide more useful information for the caregiver, such as measures of health and optimal times and methods to deliver learning information to the baby. In addition, as described above, information from sensors 721 may be accessible from mobile device 729. In various embodiments, an API interface can also be provided to third parties to allow for more applications to run on the mobile device 729.

According to various embodiments, the baby monitoring device 727 and/or monitoring hub 701 can communicate with IOS and/or Android devices. In particular, BLE is a communication stack that can be used to exchange data and upgrade firmware. In the present embodiment, the API includes access to raw data from the sensors in debug mode.

A storage API can be provided for the sensors, allowing data to be downloaded and processed by the mobile device 729 on demand.

Although not shown, a tablet device can also communicate with the monitoring hub 701 through the client device interface 717. The tablet device can serve as an accessory in the delivery of structured learning-focused interactions to the caregiver for use with the baby. In some examples, the tablet will have additional sensors useful in assessing babies' growth parameters. However, according to various embodiments, the baby is not expected to interact with the tablet during the first 24 months.

In the present example, a platform interface 719 is used to communicate with platform 731. As described above with regard to various examples, the monitoring hub 701 can send data to and receive information from platform 731. For instance, monitoring hub 701 can send raw data measurements to platform 731, and can receive models and learning materials from platform 731.

With reference to FIG. 7B, shown is a diagrammatic representation of another example of a monitoring hub. In this example, monitoring hub 735 can be a mobile device, such as a smart phone, tablet, etc. Monitoring hub 735 can provide data pre-processing, content cache, and/or baby status assessment. The monitoring hub 735 can also include learning content and schedule(s). In addition, the monitoring hub 735 can provide digital signal processing, a human interface, and data security. Furthermore, model-based content adaptation can be provided at the monitoring hub 735. Accordingly, models obtained from the platform 757 can be tailored for the baby's developmental age and needs. Specifically, development models can be evaluated at the monitoring hub 735 and content from the library can be selected and customized. One example of content adaptation as applied to interactive activities includes selecting a sequence of interactive activities that is developmentally appropriate and doesn't exhaust the baby. In particular, a determination can be made about a particular baby's developmental age and the duration of an interaction window appropriate for this age. Using this information, content from the content library stored at the platform 757 can be selected and adapted to be appropriate for the baby. This adapted content can then be presented to the baby during an appropriate interaction window.

In the present example, the monitoring hub 735 includes a processor 737, memory 739, persistent storage 741, display 743, device interface(s) 751, baby monitoring device interface 745, USB/Micro USB port 747, and platform interface 749. Although particular components are shown, it should be recognized that some of these components can be omitted without deviating from the scope of this disclosure. Additional components can also be included depending on the desired operation of the monitoring hub 735 and the baby monitoring system.

In the present embodiment, processor 737 and memory 739 can be used to process data measurements received from baby monitoring device 753. Specifically, this data can be processed to develop observations and/or inferences as described above with regard to FIG. 3. In addition, processor 737 and memory 739 can be used to customize content for the baby such as learning materials to be age appropriate. Persistent storage 741 can store content and schedule(s), as well as any models, charts, etc. received from the platform 757. Furthermore, persistent storage 757 can store information specific to the baby.

In the present example, display 743 allows a caregiver to view and or interact with the monitoring hub 735. For instance, the caregiver can view observations or inferences made about the baby, view a video feed, listen to audio from the baby's room, and input data through the display 743. In addition, notifications, alerts, suggestions, etc. can be displayed for the caregiver through the display 743.

In the present embodiment, device interface(s) 751 facilitates the operation of peripheral devices with the baby monitoring system. For instance, ambient sensing, such as local sensing of environment, vibration sensing, audio sensing, and visual monitoring may be desirable. As such, various external devices 759 can be included as part of the baby monitoring system. In particular, camera 761 can be used to transmit video for a caregiver to see on a monitor, such as through display 743. Camera 763 can also be used to gather data measurements associated with the baby such as position. Audio sensor 765 can be used to transmit audio for a caregiver to hear, such as through speakers included in the mobile device. Audio sensor 765 can also be used to gather data measurements associated with the baby's surroundings and environment. In addition, the audio sensor 765 can be used to gather data measurements about sounds from the baby, such as cries, verbal articulation, etc. In some examples, a projector 763 can be included as part of the monitoring hub 735. Projector 763 can be used to display lights or images for the baby to see. This feature can be useful to augment the environment with soothing lights, colors, or images. In some examples, this may be used to present as learning content to the baby. According to various embodiments, the external devices 759 communicate wirelessly with monitoring hub 735 through the device interface(s) 751. Because the devices are physically separate from the monitoring hub 735, these devices can be conveniently positioned relative to the baby.

In the present embodiment, a tablet device 759 (or other mobile device) can communicate with monitoring hub 735 through device interface(s) 751. The tablet device 759 can serve as an accessory in the delivery of structured learning-focused interactions to the caregiver for use with the baby. In some examples, the tablet can have additional sensors useful in assessing babies' growth parameters. For instance, tablet device 759 can be used to monitor audio or video from the baby's environment, especially when the tablet device 759 is located near the baby and the mobile device is located near the caregiver. According to various embodiments, the baby is not expected to interact with the tablet device 759 during the first 24 months.

In the present embodiment, monitoring hub 735 includes numerous interfaces. For instance, baby monitoring device interface 745 facilitates wireless communication with the baby monitoring device 753. USB/Micro USB Port 747 can be used as a plug-in for charging base 755, such as the one shown in FIG. 5C. The charging base 755 can be induction-based, such that the baby monitoring device 753 can be placed in contact with the charging base 755 during charging. In the present example, a platform interface 749 is used to communicate with platform 757. As described above with regard to various examples, the monitoring hub 735 can send data to and receive information from platform 757. For instance, monitoring hub 735 can send raw data measurements to platform 757, and can receive models and learning materials from platform 757.

In the present example, the monitoring hub 735 can be an IOS, Android, or similar device. BLE is a communication stack that can be used to exchange data and upgrade firmware. In the present embodiment, the API includes access to raw data from the sensors in debug mode. A storage API can be provided for the sensors, allowing data to be downloaded and processed by the mobile device on demand.

According to various embodiments, if a mobile device is used as a monitoring hub 735, then the baby monitoring system can be portable. As such, the monitoring system can be used outdoors, at remote locations outside of the home, etc. With this system, continuous monitoring can remain uninterrupted when the baby is taken outside or to another location. The baby monitoring device 753 can continue to transmit data to the mobile device in these embodiments. If there are other peripheral devices used for monitoring at home, such as a camera 761, audio sensor 765, or the like, that would be cumbersome or inconvenient to use while outdoors or traveling, these devices can be inactive during these outings. For instance, the monitoring system can be placed in a remote monitoring mode so that the peripheral devices, such as external devices 759 and tablet device 759, can be in a sleep mode or an energy saving mode and not transmit information during the outing.

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatuses. Accordingly, the present embodiments are to be considered as illustrative and not restrictive.

What is claimed is:

1. A system comprising:
   a first infant monitoring device associated with a plurality of biometric sensors configured to obtain biometric measurement data of an infant associated with the infant monitoring device;
   one or more environmental sensors configured to obtain environmental data from at least one of an audio feed and a video feed, the environmental sensors being separate and different from the infant monitoring device and biometric sensors; and
   a first monitoring hub configured to:
      receive biometric measurement data from the biometric sensors and environmental data from the one or more environmental sensors, and
      analyze the biometric measurement data and the environmental data in relation to a learning receptivity model obtained from a remote platform, wherein the remote platform is configured to receive information from a plurality of monitoring hubs associated with a plurality of infant monitoring devices;
   wherein the biometric measurement data and environmental data are analyzed to predict:
      a time and duration when the infant will be receptive to learning, and
      which learning content from a content library is suitable for the infant for the time and duration.

2. The system of claim 1, wherein at least one of the biometric measurement data and the environmental data comprises infant gaze intensity and duration.

3. The system of claim 1, wherein at least one of the biometric measurement data and the environmental data comprises infant position and movement.

4. The system of claim 1, wherein the learning content is customized to a developmental age associated with the infant.

5. The system of claim 1, wherein a developmental age associated with the infant is determined based on the biometric measurement data and the environmental data.

6. The method of claim 1, wherein the biometric measurement data includes motion, temperature, position, and galvanic skin response.

7. A method comprising:
   receiving biometric measurement data and environmental data at a monitoring hub,
      wherein the biometric measurement data is obtained from a plurality of biometric sensors associated with an infant monitoring device associated with an infant,
      wherein the environmental data is obtained from one or more environmental sensors from at least one of an audio feed and a video feed, the environmental sensors being separate and different from the infant monitoring device and the biometric sensors;
   analyzing the biometric measurement data and the environmental data in relation to a learning receptivity model obtained from a remote platform, the remote platform configured to receive information from a plurality of monitoring hubs associated with a plurality of infant monitoring devices; and
   based on the analyzed biometric measurement data and the analyzed environmental data, predicting:
      a time and duration when the infant will be receptive to learning; and
      which learning content from a content library is suitable for the infant for the time and duration.

8. The method of claim 7, wherein at least one of the biometric measurement data and the environmental data comprises infant gaze intensity and duration.

9. The method of claim 7, wherein at least one of the measurement data and the environmental data comprises infant position and movement.

10. The method of claim 7, further comprising presenting learning content customized to a developmental age associated with the infant.

11. The method of claim 7, further comprising determining a developmental age associated with the infant based on the biometric measurement data and the environmental data.

12. The method of claim 11, wherein predicting a time and duration is based on the developmental age associated with the infant.

13. The method of claim 7, wherein the biometric measurement data includes motion, temperature, position, and galvanic skin response.

14. The method of claim 7, wherein analyzing the biometric measurement data and the environmental data comprises processing the data into an observation about the infant and comparing the observation to the learning receptivity model.

15. The method of claim 14, wherein the observation includes one of sleep, mobility, stress, position, comfort, health, vigilance, or articulation.

16. The method of claim 7, wherein analyzing the biometric measurement data and the environmental data comprises processing the data into an inference about the infant and comparing the inference to the learning receptivity model.

17. The method of claim 16, wherein the inference includes one of receptivity to learning, infant well-being, presence of caregiver, environmental factors, safety of infant, or emotional state of infant.

18. The method of claim 10, wherein customizing learning content for the infant includes preparing informational material for a caregiver associated with the infant.

19. The method of claim 10, wherein customizing learning content for the infant includes preparing suggestions for a caregiver associated with the infant.

20. The method of claim 7, further comprising presenting learning content customized based on previous learning associated with the infant.

* * * * *